United States Patent
Dhuey

(10) Patent No.: US 6,881,253 B2
(45) Date of Patent: Apr. 19, 2005

(54) SPRAY BINDING AGENT FOR TATTOO STENCIL

(76) Inventor: Paul Dhuey, 871 Emerald St., San Diego, CA (US) 92109

( * ) Notice: Subject to any disclaimer, the term of this patent is extended or adjusted under 35 U.S.C. 154(b) by 0 days.

(21) Appl. No.: 10/814,137

(22) Filed: Apr. 1, 2004

(65) Prior Publication Data

US 2004/0221402 A1 Nov. 11, 2004

Related U.S. Application Data

(60) Provisional application No. 60/468,111, filed on May 6, 2003.

(51) Int. Cl.$^7$ .......................... C09D 5/00; C09D 191/00
(52) U.S. Cl. ................. 106/244; 8/404; 8/94.1
(58) Field of Search ............................. 106/244; 8/404, 8/94.1

(56) References Cited

U.S. PATENT DOCUMENTS

| | | |
|---|---|---|
| 2,857,315 A | 10/1958 | Kedzie |
| 3,446,683 A * | 5/1969 | Dean ........................ 156/89.24 |
| 4,169,169 A | 9/1979 | Kitabatake |
| 4,504,465 A | 3/1985 | Sampson et al. |
| 4,594,276 A | 6/1986 | Relyea |
| 5,120,541 A | 6/1992 | Macaulay et al. |
| 5,275,496 A | 1/1994 | Fattori et al. |
| 5,407,668 A | 4/1995 | Kellner |
| 5,585,092 A | 12/1996 | Trandai et al. |
| 5,639,463 A | 6/1997 | Kilpatrick-Liverman et al. |
| 5,730,963 A | 3/1998 | Hillard, Jr. et al. |
| 5,816,269 A | 10/1998 | Mohammed |
| 5,972,319 A | 10/1999 | Linn et al. |
| 6,007,799 A | 12/1999 | Lee et al. |
| 6,165,480 A | 12/2000 | Kasat et al. |
| 6,315,480 B1 | 11/2001 | Martel et al. |
| 6,428,797 B1 | 8/2002 | Fishman |

* cited by examiner

*Primary Examiner*—David Brunsman
(74) *Attorney, Agent, or Firm*—Richard C. Litman

(57) ABSTRACT

The spray binding agent for a tattoo stencil is a chemical composition useful for enhancing the quality of a tattoo when using a stencil. The liquid composition is sprayed on the cleaned skin area prior to tattooing. The composition contains a cosmetic stick composition, a green soap solution, rubbing alcohol, and water. A method of tattooing using the composition is provided which includes spraying the composition onto the body part to be tattooed.

4 Claims, No Drawings

SPRAY BINDING AGENT FOR TATTOO STENCIL

CROSS-REFERENCE TO RELATED APPLICATION

This application claims the benefit of U.S. Provisional Patent Application Ser. No. 60/468,111, filed May 6, 2003.

FIELD OF THE INVENTION

The present invention relates generally to tattoos. More specifically, the invention is a spray binding agent that enhances the ability of a tattoo stencil to temporarily adhere to a person's skin during the subsequent tattooing procedure.

DESCRIPTION OF RELATED ART

The related art of interest describes various tattooing procedures using preparations to enhance the tattooing process, but none discloses the present inventive composition. There is a need for a liquid composition that will create a more sterile environment during tattooing, thus improving the accuracy of the tattooing process. The related art will be discussed in the order of perceived relevance to the present invention.

U.S. Pat. No. 6,315,480, issued on Nov. 13, 2001 to Martel et al., describes a device for diffusing one or several fluid tattooing ink product doses, and a device for applying a temporary adhesive tattoo using the diffusing device. The first device for diffusing one or several fluid product doses is contained in sealed, flexible and ductile reserves that will burst open at a weakened zone to release the contents. The contents can be creamy, gelatinous or pasty. The devices are distinguishable for requiring an adhesive, a specific container shape and compositions dissimilar to the composition of the present invention.

U.S. Pat. No. 4,504,465, issued on Mar. 12, 1985 to Sampson et al., describes stable, single phase, soap gel, cosmetic stick compositions comprising a polyhydric aliphatic alcohol, an ethylene oxide and/or propylene condensation product and soap. The soap gel sticks are distinguishable for being limited to soap gel, cosmetic stick compositions.

U.S. Pat. No. 5,275,496, issued on Jan. 4, 1994 to Fattori et al., describes a stick package with an applicator surface comprising an antiperspirant composition. The composition is distinguishable for being limited to an antiperspirant.

U.S. Pat. No. 2,857,315, issued on Oct. 21, 1958 to W. Kedzie Teller, describes a propylene glycol soap gel stick antiperspirant composition containing a base comprising a sodium stearate-propylene glycol soap gel, alcohol, and having dispersed within sodium zirconium lactate. The composition is distinguishable for being limited to a gel stick antiperspirant composition.

U.S. Pat. No. 4,169,169, issued on Sep. 25, 1979 to Terumiti Kitabatake, describes a transfer process and a transfer sheet for patterning a design on human skin comprising a transfer sheet made of parchment paper over a blotting paper patterned with an oil dye ink composition by silk-screening. The process and ink materials are clearly distinguishable from the present invention.

U.S. Pat. No. 4,594,276, issued on Jun. 10, 1986 to Keith E. Relyea, describes printed, removable body tattoos on a translucent substrate comprising a printed image on a translucent surface of a porous, non-woven, compacted tissue substrate with an adhesive on the back-side of the substrate. The translucent qualities of the substrate enhance the visual effect of the printed image. The body tattoos are distinguishable for being limited to the tattoo carriers.

U.S. Pat. No. 5,816,269, issued on Oct. 6, 1998 to Khadija Mohammed, describes a temporary tattoo formed on the skin using a stencil mechanism that has flexibility and adhesive attachment to the skin surface. For handling and storage purposes, the flexible stencil sheet is sandwiched between a backing sheet and a protective carrier sheet. In the use of the stencil mechanism, the protective carrier sheet and stencil sheet are torn away from the backing sheet to expose an adhesive film on the stencil sheet. After the stencil sheet has been adhesively attached to the shin surface, the carrier sheet is peeled off the stencil sheet to expose the stencil openings. Colored dye is applied through the stencil openings to form a temporary tattoo. The tattoo stencil mechanism is distinguishable for requiring an adhesive film.

U.S. Pat. No. 5,836,998, issued on Nov. 17, 1998 to Mueller et al., describes an adhesive stencil for body art comprising an adhesive layer and a non-absorbent layer coextensive about a decorative pattern that is temporarily secured to the skin to allow a decorative henna-based stain to be applied. After the stain has dried, the stencil is removed. The stencil and the procedure of use are distinguishable for requiring an adhesive layer.

U.S. Pat. No. 5,120,541, issued on Jun. 9, 1992 to Macaulay et al., describes a transparent cosmetic stick composition having a lamellar structure comprising by weight %: (a) 5 to 95% alcohol; (b) 3 to 20% soap; (c) 0.1 to 10% a soap crystal growth inhibitor; and (d) up to 30% water. The composition is distinguishable for requiring a soap crystal growth inhibitor.

U.S. Pat. No. 5,407,668, issued on Apr. 18, 1995 to David M. Kellner, describes clear deodorant stick compositions based on weight % comprising 1–20% soap, 0.01–10% antibacterial agent, 10–40% water, 40–90% polyhydric alcohol, 1–10% Pentadoxynol 200, and 1–20% alkanolamide and alkoxylated alcohol (clarity stabilizers). The stick composition is distinguishable for requiring an antibacterial agent, Pentadoxynol 200, and clarity stabilizers.

U.S. Pat. No. 5,585,092, issued on Dec. 17, 1996 to Trandai et al., describes gel deodorant compositions comprising by weight: (a) 0.001–50% active deodorant and/or fragrance; (b) 0.01–15% fatty acid soap gelling agent; (c) 3–50% glycerol and/or a glycerol polymer; (d) 5–70% polyoxyethylene; (e) 8–75% water; and (f) less than 15% propylene glycol. The composition is distinguishable for requiring gel deodorant ingredients.

U.S. Pat. No. 5,639,463, issued Jun. 17, 1997 to Kilpatrick-Liverman et al., describes a clear cosmetic deodorant soft gel or stick composition comprising by weight: 55–80% propylene glycol; 9–25% water; 4–10% sodium stearate gelling agent; and 0.5–20% dimethicone copolyols. The composition is distinguishable for requiring organic ingredients not present in the present invention.

U.S. Pat. No. 5,730,963, issued on Mar. 24, 1998 to Hilliard, Jr. et al., describes a clear cosmetic gel composition having reduced skin irritation comprising by weight percent: (a) 3–10% soap; (b) up to 20% propylene glycol; (c) 40–80% polypropylene glycol; up to 0.5% hydroxydiphenyl ether; and up to 2.5% fragrance and color. The composition is distinguishable for requiring polypropylene glycol and hydroxydiphenyl ether.

U.S. Pat. No. 5,972,319, issued on Oct. 26, 1999 to Linn et al., describes an antiperspirant stick comprising by weight: 17–40% gelling agent (hydrogenated castor oil, stearyl alcohol and cyclomethicone); 30–50% solvent (volatile cyclic silicones or aliphatic hydrocarbons); a non-volatile emollient (carboxylic acid esters and alcohols); 10–30% antiperspirant active; 10–27% non-volatile emollient (carboxylic acid esters); 1–15% surfactant (ethoxylated fatty acids); 10–30% antiperspirant metal salt (quaternary ammonium salt); a bacteriostat; and an inert filler selected from the group consisting of corn starch, talc, fumed silica, inorganic clays, polyethylene and mixtures thereof. The composition is distinguishable for incorporating numerous antiperspirant stick ingredients and inert fillers not required by the present invention.

U.S. Pat. No. 6,007,799, issued on Dec. 28, 1999 to Lee et al., describes a clear cosmetic gel composition comprising a water-in-oil emulsion containing: (a) an aqueous phase having 10–35% by weight of an antiperspirant active ingredient; (b) an oil phase containing a volatile silicone fluid and a non-volatile silicone fluid; (c) 17–39% coupling agent; and (d) 0.2–2.0% alkoxylated alkyl substituted siloxane as a surface active agent. The clear cosmetic composition is distinguishable for requiring an emulsified water-in-oil composition containing silicone fluids and siloxanes.

U.S. Pat. No. 6,165,480, issued on Dec. 26, 2000 to Kasat et al., describes a cosmetic soap-gelled stick composition having stability at higher temperatures comprising by weight 20–90% of a monohydric and/or polyhydric alcohol, 5–40% water, and 2–10% of a soap gelling agent containing sodium salts of fatty acids. At least 65% by weight are alkali metal salts of fatty acids having a carbon chain length of 20 to 22 carbons. A deodorant active agent, such as a bacteriostat, is also added. The composition is distinguishable for requiring fatty acids having a carbon chain length of 20–22 and a large amount of alcohol.

U.S. Pat. No. 6,428,797, issued on Aug. 6, 2002 to Yoram Fishman, describes long-lasting liquid color lipstick compositions having an acrylates/octylacrylamide copolymer, a cellulose material, alcohol, and a colorant. The cellulose may be hydroxypropyl cellulose or isostearyl alcohol, and silica may be included in the composition. Fragrance and botanical extracts can be added. The compositions are distinguishable for being limited to lipsticks.

None of the above inventions and patents, taken either singly or in combination, is seen to describe the instant invention as claimed.

SUMMARY OF THE INVENTION

The present invention is directed to a chemical composition useful for enhancing the quality of a tattoo when using a thermal spirit stencil paper. The liquid composition is sprayed on the cleaned skin area prior to applying the stencil on a customer. The fluid composition contains a cosmetic stick composition, green soap, rubbing alcohol, and water. Utilizing the composition in the tattooing process improves the tattooing results in a more accurate definition of the tattoo.

Accordingly, it is a principal object of the invention to provide a chemical composition improving the results of applying a tattoo when utilizing a thermal spirit stencil paper.

It is another object of the invention to provide a chemical composition applied to the customer's cleaned skin before applying a thermal spirit stencil paper.

It is a further object of the invention to provide a chemical composition in a fluid state.

Still another object of the invention is to provide a chemical composition containing speed stick, green soap, rubbing alcohol, and water.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENT

The present invention is directed to a chemical composition utilized in a certain phase of a tattooing process when utilizing a thermal spirit stencil paper. The fluid composition includes 25–40% by volume cosmetic stick composition, 15–30% by volume of a green soap solution, 25–40% by volume of sterilized water, and 2–20% by volume of a rubbing alcohol solution. More specifically, in a preferred embodiment the composition is made from 12 fluid ounces (about 33%) of a Speed Stick™ composition, 8 fluid ounces (about 22%) of a green soap solution, 12 fluid ounces (about 33%) of sterilized water, and 4 fluid ounces (about 11%) of a rubbing alcohol solution.

The Speed Stick™ composition is initially obtained commercially as a solid, but dissolved for application in this process, and contains bio-degradable pure vegetable oils, glycerine and alcohol. The green soap solution is used in medical grade form by hospitals, contains an anti-bacterial ingredient, and is commercially available. Rubbing alcohol is 70% by volume isopropyl alcohol and 30% water. The extra added water can be distilled or sterilized water.

The inventive solution is utilized in a fluid form, and preferably dispensed from a spray bottle to wet the affected skin area subject to the tattooing process in the following manner. A tattoo stencil is prepared, preferably on thermal spirit stencil paper. The body part to be tattooed will initially be washed with either rubbing alcohol or a green soap solution. Then the body hair is shaved off. The inventive solution is then sprayed on to wet the area. The tattooing stencil and a thermal spirit stencil paper are then applied to the body area. The final process step is the actual tattooing of a design on the body part. After the tattoo is applied, any residual stencil may be removed with rubbing alcohol or green soap solution.

It should be made clear that the inventive solution is not an adhesive, but merely temporarily binds the stencil to the body part during the tattooing process, which enhances the subsequent tattooing procedure to result in precise and accurate tattooing.

It is to be understood that the present invention is not limited to the sole embodiment described above, but encompasses any and all embodiments within the scope of the following claims.

I claim:

1. A chemical composition for use in a tattooing process, comprising:
    25–40% by volume of a cosmetic stick containing vegetable oils, glycerin and alcohol composition;
    15–30% by volume of green soap solution;
    25–40% by volume of sterilized water; and
    2–20% by volume of rubbing alcohol;
    wherein the composition forms of fluid capable of being sprayed on a body part in order to temporarily bind a stencil to the body part to guide a needle during tattooing.

2. A method of tattooing, comprising the steps of:
    preparing a tattoo stencil;
    washing a body part;
    shaving body hair from the body part;
    spraying a stencil binding composition on the body part to wet the body part;
    applying the tattoo stencil and thermal spirit stencil paper to the wetted body part;
    tattooing the body part using the stencil as a guide.

3. The method of tattooing according to claim 2, wherein the stencil binding composition consists essentially of:
    25–40% by volume of a cosmetic stick containing vegetable oils, glycerin and alcohol composition;
    15–30% by volume of green soap solution;
    25–40% by volume of sterilized water; and
    2–20% by volume of rubbing alcohol.

4. The method of tattooing according to claim 2, wherein the tattoo stencil is prepared on thermal spirit stencil paper.

* * * * *